United States Patent
Daniel

(10) Patent No.: US 9,956,253 B2
(45) Date of Patent: May 1, 2018

(54) PLACENTAL TISSUE GRAFTS

(71) Applicant: MiMedx Group, Inc., Marietta, GA (US)

(72) Inventor: John Daniel, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days. days.

(21) Appl. No.: 14/881,536

(22) Filed: Oct. 13, 2015

(65) Prior Publication Data

US 2016/0030634 A1     Feb. 4, 2016

Related U.S. Application Data

(63) Continuation of application No. 14/222,510, filed on Mar. 21, 2014, now Pat. No. 9,433,647, which is a continuation of application No. 13/954,974, filed on Jul. 30, 2013, now Pat. No. 8,709,494, which is a continuation of application No. 13/569,095, filed on Aug. 7, 2012, now Pat. No. 8,597,687, which is a continuation of application No. 11/840,728, filed on Aug. 17, 2007, now Pat. No. 8,372,437.

(60) Provisional application No. 60/838,467, filed on Aug. 17, 2006.

(51) Int. Cl.
| | |
|---|---|
| *A61K 35/50* | (2015.01) |
| *A61L 27/36* | (2006.01) |
| *A61L 27/40* | (2006.01) |
| *A61J 1/00* | (2006.01) |
| *A61L 27/54* | (2006.01) |
| *A61L 27/58* | (2006.01) |
| *A61F 2/02* | (2006.01) |
| *A61L 27/50* | (2006.01) |
| *B65D 25/20* | (2006.01) |
| *B65D 81/18* | (2006.01) |
| *B65D 85/00* | (2006.01) |

(52) U.S. Cl.
CPC .............. *A61K 35/50* (2013.01); *A61F 2/02* (2013.01); *A61J 1/00* (2013.01); *A61L 27/3604* (2013.01); *A61L 27/3683* (2013.01); *A61L 27/3687* (2013.01); *A61L 27/3691* (2013.01); *A61L 27/3695* (2013.01); *A61L 27/40* (2013.01); *A61L 27/50* (2013.01); *A61L 27/54* (2013.01); *A61L 27/58* (2013.01); *B65D 25/205* (2013.01); *B65D 81/18* (2013.01); *B65D 85/70* (2013.01); *A61L 2300/412* (2013.01); *A61L 2300/60* (2013.01); *A61L 2300/64* (2013.01); *A61L 2430/40* (2013.01)

(58) Field of Classification Search
None
See application file for complete search history.

(56) References Cited

U.S. PATENT DOCUMENTS

| | | |
|---|---|---|
| 4,361,552 A | 11/1982 | Baur, Jr. |
| 4,446,234 A | 5/1984 | Russo et al. |
| 4,846,165 A | 7/1989 | Hare et al. |
| 5,197,976 A | 3/1993 | Herweck et al. |
| 5,336,616 A | 8/1994 | Livesey et al. |
| 5,350,583 A | 9/1994 | Yoshizato et al. |
| 5,580,923 A | 12/1996 | Yeung et al. |
| 5,607,590 A | 3/1997 | Shimizu |
| 5,612,028 A | 3/1997 | Sackier et al. |
| 5,618,312 A | 4/1997 | Yui et al. |
| 5,711,969 A | 1/1998 | Patel et al. |
| 5,882,929 A | 3/1999 | Fofonoff et al. |
| 5,885,619 A | 3/1999 | Patel et al. |
| 5,916,266 A | 6/1999 | Yui et al. |
| 5,955,110 A | 9/1999 | Patel et al. |
| 5,968,096 A | 10/1999 | Whitson et al. |
| 5,997,575 A | 12/1999 | Whitson et al. |
| 6,102,946 A | 8/2000 | Nigam |
| 6,143,315 A | 11/2000 | Wang et al. |
| 6,146,414 A | 11/2000 | Gelman |
| 6,152,142 A | 11/2000 | Tseng |

(Continued)

FOREIGN PATENT DOCUMENTS

| | | |
|---|---|---|
| CN | 1757717 | 4/2006 |
| CN | 101088479 | 12/2007 |

(Continued)

OTHER PUBLICATIONS

Adams et.al. "Methods in Molecular Biology Cryopreservation and Freeze-Drying Protocols", pp. 15-72 (John G. Say & Glyn N. Stacey eds., 2nd ed., 2007).

Baergen, Rebecca N., Manual of Benirschke and Kaufmann "Pathology of the Human Placenta", pp. 80-95 (Springer 2005).

Barron's Dictionary of Medical Terms, definition of "Mucus", (6th Ed. 2013) p. 379.

Benirscke et al., "Pathology of the Human Placenta", pp. 281-334 (Springer 4th ed. 2000).

Bhatia; et al., "The Mechanism of Cell Interaction and Response on Decellularized Human Amniotic Membrane: Implications in Wound Healing," http://www.woundsresearch.com/article/7614, May 7, 2008, pp. 1-24.

(Continued)

*Primary Examiner* — Allison Fox
(74) *Attorney, Agent, or Firm* — Alston & Bird LLP

(57) ABSTRACT

A method for preparing placenta membrane tissue grafts for medical use, includes obtaining a placenta from a subject, cleaning the placenta, separating the chorion tissue from the amniotic membrane, mounting a selected layer of either the chorion tissue or the amniotic membrane onto a drying fixture, dehydrating the selected layer on the drying fixture, and cutting the selected layer into a plurality of tissue grafts. Preferably, the drying fixture includes grooves or raised edges that define the outer contours of each desired tissue graft, after they are cut, and further includes raised or indented logos that emboss the middle area of the tissue grafts during dehydration and that enables an end user to distinguish the top from the bottom side of the graft. The grafts are comprised of single layers of amnion or chorion, multiple layers of amnion or chorion, or multiple layers of a combination of amnion and chorion.

7 Claims, 5 Drawing Sheets

(56) References Cited

U.S. PATENT DOCUMENTS

| | | |
|---|---|---|
| 6,326,019 B1 | 12/2001 | Tseng |
| 6,379,710 B1 | 4/2002 | Badylak |
| 6,398,797 B2 | 6/2002 | Bombard et al. |
| 6,544,289 B2 | 4/2003 | Wolfinbarger et al. |
| 6,573,249 B2 | 6/2003 | Lezdey et al. |
| 6,576,618 B1 | 6/2003 | Herndon et al. |
| 6,581,993 B2 | 6/2003 | Nigam |
| 6,666,892 B2 | 12/2003 | Hiles et al. |
| 6,762,025 B2 | 7/2004 | Cubicciotti |
| 7,045,148 B2 | 5/2006 | Hariri |
| 7,049,139 B2 | 5/2006 | Tan et al. |
| 7,063,726 B2 | 6/2006 | Crouch et al. |
| 7,101,710 B2 | 9/2006 | Tsai et al. |
| 7,244,444 B2 | 7/2007 | Bates |
| 7,311,904 B2 | 12/2007 | Hariri |
| 7,311,905 B2 | 12/2007 | Hariri |
| 7,347,876 B2 | 3/2008 | Tsai |
| 7,407,480 B2 | 8/2008 | Staskin et al. |
| 7,413,734 B2 | 8/2008 | Mistry et al. |
| 7,494,802 B2 | 2/2009 | Tseng et al. |
| 7,498,171 B2 | 3/2009 | Hariri et al. |
| 7,569,385 B2 | 8/2009 | Haas |
| 7,611,895 B2 | 11/2009 | Tan et al. |
| 7,704,544 B2 | 4/2010 | Pacetti et al. |
| 7,727,550 B2 | 6/2010 | Siegal et al. |
| 7,815,923 B2 | 10/2010 | Johnson et al. |
| 7,824,671 B2 | 11/2010 | Binder et al. |
| 7,871,646 B2 | 1/2011 | Ghinelli |
| 7,905,826 B2 | 3/2011 | Case et al. |
| 7,915,039 B2 | 3/2011 | Teplyashin |
| 7,919,112 B2 | 4/2011 | Pathak et al. |
| 7,928,280 B2 | 4/2011 | Hariri et al. |
| 7,968,336 B2 | 6/2011 | Atala et al. |
| 7,976,836 B2 | 7/2011 | Hariri |
| 7,993,918 B2 | 8/2011 | Paludan et al. |
| 8,021,876 B2 | 9/2011 | Atala et al. |
| 8,039,256 B2 | 10/2011 | Sakai et al. |
| 8,071,135 B2 | 12/2011 | Liu et al. |
| 8,071,376 B2 | 12/2011 | Heidaran |
| 8,105,634 B2 | 1/2012 | Liu et al. |
| 8,153,162 B2 | 4/2012 | Tseng et al. |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,268,302 B2 | 9/2012 | Weiss et al. |
| 8,287,854 B2 | 10/2012 | Phan |
| 8,323,701 B2 | 12/2012 | Daniel et al. |
| 8,338,175 B2 | 12/2012 | Devi et al. |
| 8,357,403 B2 | 1/2013 | Daniel et al. |
| 8,367,409 B2 | 2/2013 | Abbot et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,409,626 B2 | 4/2013 | Daniel et al. |
| 8,414,929 B2 | 4/2013 | Nikaido et al. |
| 8,455,251 B2 | 6/2013 | Ra et al. |
| 8,460,715 B2 | 6/2013 | Daniel |
| 8,460,716 B2 | 6/2013 | Daniel |
| 8,597,687 B2 | 12/2013 | Daniel |
| 8,642,092 B2 | 2/2014 | Daniel et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,840,665 B2 | 9/2014 | Young et al. |
| 8,904,664 B2 | 12/2014 | Pringle et al. |
| 8,932,620 B2 | 1/2015 | Lelkes et al. |
| 8,932,641 B2 | 1/2015 | Nikaido et al. |
| 8,932,643 B2 | 1/2015 | Daniel et al. |
| 9,056,093 B2 | 6/2015 | Atala et al. |
| 9,084,767 B2 | 7/2015 | Daniel et al. |
| 9,186,382 B2 | 11/2015 | Daniel et al. |
| 9,205,177 B2 | 12/2015 | Schorgl et al. |
| 9,272,003 B2 | 3/2016 | Daniel et al. |
| 9,533,011 B2 | 1/2017 | Daniel et al. |
| 2001/0053839 A1 | 12/2001 | Noishiki et al. |
| 2001/0056303 A1 | 12/2001 | Caneiro et al. |
| 2002/0039788 A1 | 4/2002 | Isseroff et al. |
| 2002/0103542 A1 | 8/2002 | Bilbo |
| 2002/0128222 A1 | 9/2002 | Herndon et al. |
| 2003/0032179 A1 | 2/2003 | Hariri |
| 2003/0187515 A1 | 10/2003 | Hariri et al. |
| 2003/0235580 A1 | 12/2003 | Zhang |
| 2004/0028660 A1 | 2/2004 | Hariri et al. |
| 2004/0048796 A1 | 3/2004 | Hariri et al. |
| 2004/0057938 A1 | 3/2004 | Ghinelli |
| 2004/0126878 A1 | 7/2004 | Ramos et al. |
| 2004/0171147 A1 | 9/2004 | Hariri |
| 2004/0219136 A1 | 11/2004 | Hariri |
| 2004/0265293 A1 | 12/2004 | Crowe et al. |
| 2005/0026279 A1 | 2/2005 | Tseng et al. |
| 2005/0027356 A1 | 2/2005 | Fishman et al. |
| 2005/0042595 A1 | 2/2005 | Haas |
| 2005/0089513 A1 | 4/2005 | Sakuragawa et al. |
| 2005/0107876 A1 | 5/2005 | Kim et al. |
| 2005/0118715 A1 | 6/2005 | Hariri et al. |
| 2005/0148034 A1 | 7/2005 | Hariri et al. |
| 2005/0244963 A1 | 11/2005 | Teplyashin |
| 2005/0287223 A1 | 12/2005 | Peyman |
| 2006/0004189 A1 | 1/2006 | Gandy |
| 2006/0147492 A1 | 7/2006 | Hunter et al. |
| 2006/0153815 A1 | 7/2006 | Seyda et al. |
| 2006/0153928 A1 | 7/2006 | Kinoshita et al. |
| 2006/0222634 A1 | 10/2006 | Clarke et al. |
| 2006/0228339 A1 | 10/2006 | Wang |
| 2006/0281178 A1 | 12/2006 | Sakuragawa et al. |
| 2007/0020225 A1 | 1/2007 | Abramson et al. |
| 2007/0021762 A1 | 1/2007 | Liu et al. |
| 2007/0025973 A1 | 2/2007 | Fitzsimmons et al. |
| 2007/0031471 A1 | 2/2007 | Peyman |
| 2007/0038298 A1 | 2/2007 | Sulner et al. |
| 2007/0048292 A1 | 3/2007 | Morita et al. |
| 2007/0116682 A1 | 5/2007 | Atala et al. |
| 2007/0116684 A1 | 5/2007 | Atala et al. |
| 2007/0122903 A1 | 5/2007 | Rezania et al. |
| 2007/0128719 A1 | 6/2007 | Tseng et al. |
| 2007/0142745 A1 | 6/2007 | Brahm |
| 2007/0190042 A1 | 8/2007 | Edinger et al. |
| 2007/0254013 A1 | 11/2007 | Taguchi et al. |
| 2007/0269791 A1 | 11/2007 | Takami et al. |
| 2007/0292401 A1 | 12/2007 | Harmon et al. |
| 2008/0032401 A1 | 2/2008 | Edinger et al. |
| 2008/0039940 A1 | 2/2008 | Hashimoto et al. |
| 2008/0044848 A1 | 2/2008 | Heidaran |
| 2008/0069895 A1 | 3/2008 | Liu et al. |
| 2008/0102135 A1 | 5/2008 | Ollivier |
| 2008/0113007 A1 | 5/2008 | Kurihara et al. |
| 2008/0131522 A1 | 6/2008 | Liu et al. |
| 2008/0159999 A1 | 7/2008 | Stefanidis |
| 2008/0181935 A1 | 7/2008 | Bhatia et al. |
| 2008/0193554 A1 | 8/2008 | Dua et al. |
| 2008/0233552 A1 | 9/2008 | Ma et al. |
| 2010/0015712 A1 | 1/2010 | Sakuragawa et al. |
| 2010/0254954 A1 | 10/2010 | Sakuragawa et al. |
| 2010/0330672 A1 | 12/2010 | Sakuragawa et al. |
| 2011/0129520 A1 | 6/2011 | Bogdansky et al. |
| 2011/0189301 A1 | 8/2011 | Yang et al. |
| 2011/0206776 A1 | 8/2011 | Tom et al. |
| 2011/0212158 A1 | 9/2011 | Tom et al. |
| 2011/0256202 A1 | 10/2011 | Tom et al. |
| 2011/0293691 A1 | 12/2011 | Weber et al. |
| 2012/0294910 A1 | 11/2012 | Daniel et al. |
| 2013/0344162 A1 | 12/2013 | Morse et al. |
| 2014/0050788 A1 | 2/2014 | Daniel et al. |
| 2014/0052274 A1 | 2/2014 | Koob et al. |
| 2014/0343688 A1 | 11/2014 | Morse et al. |

FOREIGN PATENT DOCUMENTS

| | | |
|---|---|---|
| EP | 0773033 A1 | 5/1997 |
| EP | 2197270 B1 | 12/2016 |
| FR | 2892311 | 4/2007 |
| JP | 08-266613 | 10/1996 |
| JP | 2001-161353 | 6/2001 |

(56) References Cited

FOREIGN PATENT DOCUMENTS

| | | |
|---|---|---|
| WO | WO-93/10722 | 6/1993 |
| WO | WO-2005/007835 A1 | 1/2005 |
| WO | WO-2005/075002 | 8/2005 |
| WO | WO 2006/129673 | 12/2006 |
| WO | WO-2007/010305 | 1/2007 |
| WO | WO-2007/013331 | 2/2007 |
| WO | WO 2009/033160 | 3/2009 |
| WO | WO 2009/132186 | 10/2009 |
| WO | WO 2012/112441 | 8/2012 |

OTHER PUBLICATIONS

Bourne, G., "The Foetal Membranes. A Review of the Anatomy of Normal Amnion and Chorion and Some Aspects of their Function", Postgrad Med J. 1962, 38:193-201.
Bourne, G., "The Microscopic Anatomy of the Human Amnion and Chorion", Am. J. Obstet. & Gynec., 1960, vol. 79, No. 6, pp. 1070-1073.
Burgos, "Angiogenic and growth factors in human amnio-chorion and placenta", European Journal of Clinical Investigation (1983) 13, 289-296.
Certified English-Language Translation of CN 1757717A to Wei He, 14 pages.
Certified English-Language Translation of JP 2001-161353 to Shimazaki, 10 pages.
Certified English-Language Translation of WO 2005/075002 to Taguchi et al., 22 pages.
Certified English-Language Translation of WO 2007/013331 to Kinoshita et al., 107 pages.
Declaration of Daniel L. Mooradian, Ph.D. in Inter Partes Review No. 2015-00320, U.S. Pat. No. 8,709,494, dated Nov. 21, 2014.
Declaration of Helen N. Jones, Ph.D., in Inter Partes Review No. 2015-00664, U.S. Pat. No. 8,372,437, dated Feb. 2, 2015.
Dino et al., "Human Amnion: The Establishment of an Amnion Bank and its Practical Applications in Surgery", The Journal of the Philippine Medical Association, Jul. 1966, vol. 42, No. 7, pp. 357-366.
Dioguardi et al., "Skin Substitutes in Burn Treatment—Our Experience", Annals of the Medit. Burns Club—vol. 3, No. 4, Dec. 1990, 7 pages.
Dorlands Illustrated Medical Dictionary, "Denude" [accessed on 2015].
Douglas, "Homografts of Fetal Membranes as a Covering for Large Wounds-Especially Those from Burns, an experimental and clinical study (a preliminary report)", The Journal of the Tennessee State Medical Association, 1952, vol. 45, No. 6, pp. 230-235.
Dua et al., "Amniotic membrane transplantation", Br. J. Ophthalmol., 1999, 83:748-752.
Ebihara, et al., "The Functions of Exogenous and Endogenous Laminin-5 on Corneal Epithelial Cells," Exp. Eye Res., 2000, 71:69-79.
Farazdaghi et al., "Electron Microscopy of Human Amniotic Membrane, Advances in Tissue Banking", The Scientific Basis of Tissue Transplantation, 2001, vol. 5, pp. 149-171.
File history of U.S. Pat. No. 8,372,437, U.S. Appl. No. 11/840,728, 324 pages.
File History of U.S. Pat. No. 8,709,494, U.S. Appl. No. 13/954,974, 180 pages.
Fukuda, et al., "Differential Distribution of Subchains of the Basement Membrane Components Type IV Collagen and Laminin Among the Amniotic Membrane, Cornea, and Conjuctiva," Cornea, (1999), 18(1):73-79.
Gartner & Hiatt, Color Textbook of Histology (2nd ed. W. B. Saunders Co., 2001)(Part 1).
Gartner & Hiatt, Color Textbook of Histology, (2nd ed. W. B. Saunders Co. 2001) (Part 2).
Gilbert et al., "Decellularization of tissues and organs", Biomaterials, 2006, 27:3675-3683.
Hanada et al., "Multilayered Amniotic Membrane Transplantation for Severe Ulceration of the Cornea and Sclera", American Journal of Ophthalmology, Mar. 2001, vol. 131, No. 3, pp. 324-331.

Hao, et al., "Identification of Antiangiogenic and Antiinflammatory Proteins in Human Amniotic Membrane," Cornea, (2000). 19(3):348-352.
Ishino et al., "Amniotic Membrane as a Carrier for Cultivated Human Corneal Endothelial Cell Transplantation, Investigative Ophthalmology & Visual Science", Mar. 2004, vol. 45, No. 3, pp. 800-806.
Klen (Hradec Kralove) "Preparation of chorion and/or amnion grafts used in burns", Chapter Five, International Congress on Research in Burns, 3d, Prague, 1970, pp. 289-292.
Koizumi, et al., "Growth Factor mRNA and protein in preserved human amniotic membrane," Current Eye Reserach, (2000), 20(3):173-177.
Koob et al., "Angiogenic properties of dehydrated human amnion/chorion allografts: therapeutic potential for soft tissue repair and regeneration", Vascular Cell, (2014) (http://www.vascularcell.com/content/6/1/10).
Koob et al., "Biological Properties of dehydrated human amnio/chorion composite graft: Implications for chronic wound healing", 2013, Intl. Wound J., pp. 493-500.
Koob et al., "Properties of Dehydrated Human Amnion/Chorion Composite Grafts: Implications for Wound Repair and Soft Tissue Regeneration", J. Biomed Mater Res Part B, 2014, pp. 80-95.
Lee et al., "Amniotic Membrane Transplantation for Persistent Epithelial Defects with Ulceration", American Journal of Ophthalmology, 1997, vol. 123, No. 3, pp. 303-312.
Maan et al., "Cell recruitment by amnion chorion grafts promotes neovascularization", J. Surg. Res., Jan. 2015, 193, pp. 953-962.
Malak et al., "Confocal Immunofluorescence Localization of Collagen Types I, III, IV, V and VI and Their Ultrastructural Organization in Term Human Fetal Membranes", Placenta, 1993, 14:385-406.
McGraw-Hill Online Learning Center Test, Placenta, retrieved from the Internet at: http://www.mhhe.com/cgi-bin/netquiz_get.pl?qfooter=/usr/web/home/mhhe/biosci/genbio/maderbiology7/student/olc/art_quizzes/0565fq.htm&afooter=/usr/web/home/mhhe/biosci/genbio/maderbiology7/student/olc/art_quizzes/0565fa.htm&test=/usr/web/home/mhhe/biosci/genbio/naderbiology7/student/olc/art_quizzes/0565q.txt&answers=/usr/web/home/mhhe/biosci/genbio/maderbiology7/student/olc/art_quizzes/0565a.txt on Jan. 28.
Merriam-Webster Collegiate Dictionary, (11th ed. 2003)—"Intact".
Merriam-Webster Dictionary, Definition of "Dehydrate", (New Ed. 2005) p. 129.
Merriam-Webster Dictionary, Definition of "Laminate", (New Ed. 2005) p. 277.
Merriam-Webster Online Dictionary, "Denude" [accessed on 2015].
Merriam-Webster Online Dictionary, "Laminate".
Miljudin et al., "Silicia Gel Dissication of Amniotic Membrane with Related Epithelium Cells for Ocular Surface Reconstruction", 2004 Cell Tissue Bank., 5:271 pp. 271-275.
*MiMedx Group, Inc. v. Liventa Bioscience, Inc, et al.*, 1:14-cv-1178, N. D. GA., Joint Claim Construction Statement, Exhibit D, dated Dec. 15, 2014.
*MiMedx Group, Inc. v. Liventa Bioscience, Inc. et al.*, 1:14-cv-1178, N.D. GA, Expert Declaration of Rebecca N. Baergen, , dated Dec. 15, 2014.
*MiMedx Group, Inc. v. Liventa Bioscience, Inc. et al.*, 1:14-cv-1178, N.D. GA, Rebuttal Expert Declaration of Rebecca N. Baergen, M.D., dated Feb. 6, 2015.
*MiMedx Group, Inc. v. Liventa Bioscience, Inc., et al.*, Case No. 14-cv-01178—MHC, Plaintiff's Opening Claim Construction Brief, Dkt. No. 112, dated Feb. 20, 2015.
*MiMedx Group, Inc. v. Liventa Bioscience, Inc. et al.*, 1:14-cv-1178, N.D. GA., Joint Claim Construction Statement, dated Dec. 15, 2014.
*MiMedx Group, Inc. v. Nutech Medical, Inc. et al.*, Case 2:15-CV-0369-VEH Memorandum Opinion and Order, Nov. 24, 2015, 19 pages.
*MiMedx Group, Inc. vs. Liventa Bioscience, Inc. et al.*, 14-cv-01178, Complaint in Civil Action for Infringement in filed Apr. 21, 2014, 62 pages.
Niknejad, et al., "Properties of the Amniotic Membrane for Potential Use in Tissue Engineering," European Cells and Materials, (2008), 15:88-99.

(56) References Cited

OTHER PUBLICATIONS

Non-Final Office Action on U.S. Appl. No. 10/397,867, dated Jan. 23, 2009, 9 pages.
Ohno-Matsui et al., "In vitro and in vivo characterization of iris pigment epithelial cells cultured on amniotic membranes", Molecular Vision 2006; 12:1022-32.
Oxlund et al., "Biomechanical analysis of human chorioamniotic membranes", European Journal of Obstetrics & Gynecology and Reproductive Biology, 1990, 34, pp. 247-255.
Pakkala, et al., "Function of Laminins and Laminin-Binding Integrins in Gingival Epithelial Cell Adhesion," J. Periodontol, (2002), 709-719.
Park, et al., "Healing of a porcine burn wound dressed with human and bovine amniotic membranes," Wound Rep. Reg., 2008, 16:520-528.
Parry et al., "Premature Rupture of the Fetal Membranes, Mechanisms of Disease", The New England Journal of Medicine, 1998, vol. 338, No. 10, pp. 663-670.
Patent Owner's Preliminary Response for Inter Partes Review 2015-00664, U.S. Pat. No. 8,372,437 dated May 20, 2015.
Patent Owner's Preliminary Response to Petition for Inter Partes Review 2015-00320 of U.S. Pat. No. 8,709,494, dated Mar. 30, 2015.
Petition for Inter Partes Review of U.S. Pat. No. 8,372,437, dated Feb. 2, 2015, IPR2015-00664.
Petition for Inter Partes Review of U.S. Pat. No. 8,709,494 from Petitioner, Tissue Transplant Technology Ltd. & Human Biologics of Texas Ltd., dated Dec. 1, 2014, IPR2015-00320.
Placenta, retrieved from the Internet at www.uwyo.edu/wjm/repro/placenta.htm on Nov. 6. 2014.
Poser; Bone Bank Allografts Research Report Feb. 2014, Oct. 14, 2014, 2 pages.
Rinastiti et al., "Histological evaluation of rabbit gingival wound healing transplanted with human amniotic membrane", International Journal of Oral and Maxillofacial Surgery, 2006: 35:247-251.
Robson et al., "Amniotic Membranes as a Temporary Wound Dressing, Surgery", Gynecology & Obstetrics, Jun. 1973, vol. 136, pp. 904-906.
Selected excerpts of Prosecution History of U.S. Pat. No. 8,709,494. 111 pages.
Selected Excerpts of the prosecution history of U.S. Appl. No. 11/840,728, 74 pages.
Takashima, et al., "Characterization of laminin isoforms in human amnion," Tissue and Cell, (2008), 40:75-77.
Talmi, et al., "Antibacterial Properties of Human Amniotic Membranes," Placenta, 1991, 12:285-288.
Toda et al., "The Potential of Amniotic Membrane/Amnion-Derived Cells for Regeneration of Various Tissues", Journal of Pharmacological Sciences, 2007, 105, pp. 215-228.
Vicovac et al., "Epithelia-Mesenchymal Transition during Trophoblast Differentiation", Acta Anat., 1996, 156:202-216.
Vishwakarma, et al., "Amniotic Arthroplasty for Tuberculosis of the Hip, A Preliminary Clinical Study", The Journal of Bone and Joint Surgery, Jan. 1986, vol. 68 B, No. 1, pp. 68-74.
Volkov, M.V., "Anthroplasty of Joints Using Amniotic Membrane", Arthroplasty of the Hip, 1972, pp. 53-56.
Ward et al., "The healing of chronic venous leg ulcers with prepared human amnion", British Journal of Plastic Surgery, 1989, 42, pp. 463-467.
Zelen et al, "A prospective randomized comparative parallel study of amniotic membrane wound graft in the management of diabetic foot ulcers", Int. Wound J., 2013, pp. 502-507.
Zelen et al., "A prospective randomized comparative study of weekly versus biweekly application of dehydrated human amnion/chorion membrane allograft in the management of diabetic foot ulcers", Int. Wound J., 2014, pp. 122-128.
Zelen et al., "Dehydrated human amnion/chrion membrane allografts in patients with chronic diabetic foot ulcers: A long-term follow-up study", Wound Medicine, 2014 4:1-4.

AmnioClear product brochure, copyright 2012 http://liventabioscience.com/assets/amnioclear_brochure.pdf.
AmnioClear product brochure, copyright 2014, http://liventabioscience.com/assets/liventabrochure.pdf.
Bailey, Neal, "Soft Contact Lens Identification", Nov. 1975, Journal of the American Optometric Association, vol. 46, No. 11, pp. 1177-1178.
Declaration of John Daniel in U.S. Appl. No. 13/569,131 dated Jan. 28, 2013.
Dictionary.com—"Asymmetric" http://dictionary.reference.com/browse/asymmetric; Apr. 13, 2015.
Fink et al., "Influence of Rigid Contact Lens Overall and Optic Zone Diameters on Tear Pump Efficiency", 1990, Optometry and Vision Science, vol. 67, No. 8, pp. 641-644.
Hollick, Emily, "Intraocular Lens Implantation", www.optometry.co.uk, Nov. 2, 2001.
IPR2015-00420 Patent Owner's Corrected Notice of Deposition of Daniel Mooradian, Aug. 31, 2015.
IPR2015-00420, Decision Institution of Inter Partes Review, Jul. 10, 2015.
IPR2015-00420, Declaration of Roy Chuck, M.D., Ph.D., Oct. 12, 2015.
IPR2015-00420, Transcript of the Sep. 9-10, 2015 Deposition of Daniel Mooradian, Ph.D.
Merriam-Webster Online Dictionary—"Indent"; Feb. 2, 2015.
MTF Dry Amniotic Membrane product information sheet, Mar. 2014, http://www.mtf.org/documents/Pl_-89 Rev 6.pdf.
MTF Dry Amniotic Membrane Product Information Sheet, Oct. 2012, http://www.mtf.org/documents/Pl_-89 Rev 2.pdf.
Patent Owner's Preliminary Response to Petition for Inter Partes Review 2015-00420, dated Apr. 13, 2015.
Patent Owner's Response for U.S. Pat. No. 8,597,687 in IPR2015-00420 dated Oct. 13, 2015.
Thomsen, Sharon, "Pathologic Analysis of Photothermal and Photochemical Effects of Laser-Tissue Interactions", 1991, Photochemistry and Photobiology, vol. 53, No. 6, pp. 825-835.
Transcript of the Jan. 27, 2013 Deposition of Daniel Mooradian, 14-CV-00719-HLH.
VersaShield brochure, Mar. 2013, https://web.archive.org/web/20130719054832/http:/us.orthofix.com/common_products.asp?pid=106&cid?48.
VersaShield Products and Tissue Forms, Oct. 2015, http://web.orthofix.com/Products/Pages/VersaShield.aspx?catid=27.
Non-Final Office Action for U.S. Appl. No. 13/569,131 dated Oct. 2, 2012.
Notice of Allowance for U.S. Appl. No. 13/569,131 dated Mar. 21, 2013.
Amendment and Reply Under 37 CFR 1.111 for U.S. Appl. No. 13/569,131 dated Jan. 2, 2013.
International Search Report dated May 30, 2012 for International Application No. PCT/US12/24858.
International Search Report and Written Opinion dated Nov. 13, 2008 in related PCT Application No. PCT/US2008/75608.
U.S. Office Action dated Dec. 8, 2011, in related U.S. Appl. No. 12/428,908.
U.S. Appl. No. 60/696,167 filed Jun. 30, 2005.
U.S. Appl. No. 60/970,780 filed Sep. 14, 2008 inventor: Tofe.
U.S. Appl. No. 60/986,665 filed Nov. 9, 2007 inventor: Daniel.
U.S. Appl. No. 60/989,299 filed Nov. 20, 2007 inventor: Tofe, et al.
Rodriquez-Ares, et al., "Effects of lyophilization on human amniotic membrane," Acta Ophthalmol,. 2009, vol. 87, pp. 396-403.
Bose, B., "Burn wound dressing with human amniotic membrane," Annals of the Royal College of Surgeons of England, 1979, pp. 444-447, vol. 61.
Cooper, L.J., et al., "An Investigation into the Composition of Amniotic Membrane Used for Ocular Surface Reconstruction," Cornea, Aug. 2005, pp. 722-729, vol. 24, No. 6.
Dua, H.S., et al., "Controversies and Limitations of Amniotic Membrane in Ophthalmic Surgery," Essentials in Ophthalmic Cornea and External eye Disease, 2006, pp. 21-33, Chapter 2.

(56) References Cited

OTHER PUBLICATIONS

Grauss, R.W., et al., "Histological evaluation of decellurised porcine aortic valves: matrix changes due to different decellularisation methods," European Journal of Cardiothoracic Surgery, 2005, pp. 566-571, vol. 27.

Klen, R., et al., "A comparison of Dermo-Epithelial and Chorion-Amniotic Grafts in the Treatment of Burns," Acta Chirurgiae Plasticae, Apr. 18, 1976, pp. 225-232.

Rieder, E., et al., "Decellularization protocols of porcine heart valves differ importantly in efficiency of cell removal and susceptibility of the matrix to recellularization with human vascular cells," The Journal of Thoracic and Cardiovascular Surgery, 2003, pp. 399-405, vol. 127, No. 2.

Schor, S.L., "The Effects of EGTA and Trypsin on the Serum Requirements for Cell Attachment to Collagen," J. Cell. Sci., 1979, pp. 271-279, vol. 40.

Side. (n.d.). The American Heritage Dictionary of Idioms by Christine Ammer. Retrieved Feb. 24, 2017 from Dictionary.com website http://www.dictionary.com/browse/side.

Petition for Inter Partes Review of U.S. Pat. No. 8,597,687 from Petitioner, Tissue Transplant Technology Ltd. & Human Biologics of Texas Ltd., dated Dec. 11, 2014.

John, "Human amniotic membrane transplantation: Past, present and future," Ophthal. Clin. N. Am., vol. 16, No. 1, pp. 43-65 (Mar. 2003).

Koob, et al., "A Primer on Amniotic Membrane Regenerative Healing, Chapter 2: Amniotic Membrane Allografts for Tissue Repair," 14-3, MiMedx Group, Inc. (2015).

Decision of Institution of *Inter Partes*Review in IPR2015-00664, entered Aug. 18, 2015.

Patent Owner's Response in IPR2015-00664, filed Nov. 19, 2015.

Petitioner's Reply to Patent Owner's Response to Petition in IPR2015-00664, filed Feb. 10, 2016.

Final Written Decision in IPR2015-00664, filed Aug. 16, 2016.

Final Written Decision in IPR2015-00420, filed Jul. 7, 2016.

Decision Denying Institution of *Inter Partes Review*in IPR2015-00320, entered Jun. 29, 2015.

Reexamination Order in U.S. Appl. No. 90/013,986 dated Aug. 4, 2017.

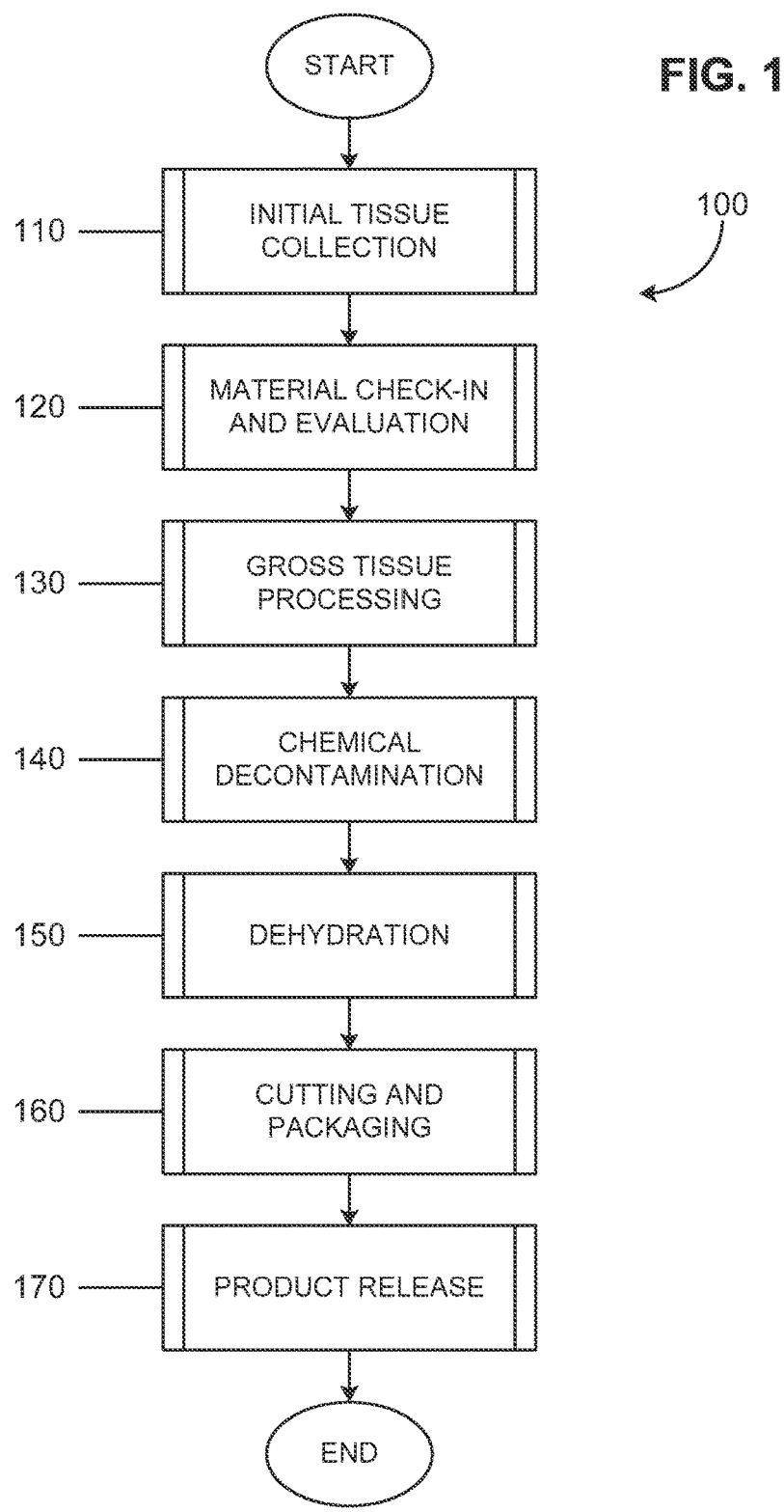

Tissue Check-In Form

FIG. 2

Tissue ID: _____ Date: _____ Time: _____

Inspect Shipment:

| | | |
|---|---|---|
| Is the shipping container sealed and intact? | ☐ Yes | ☐ No |
| Is ice or other coolant present and is contents cool? | ☐ Yes | ☐ No |
| Is donor paperwork present? | ☐ Yes | ☐ No |
| Does donor number on paperwork and tissue ID correspond? | ☐ Yes | ☐ No |

Log Tissue into Refrigerator Log:

Complete ☐ Yes ☐ No

Shipment Accepted: ☐ Accept
☐ Reject

By: _____ Date: _____

Reason for Rejection: _____

Comments: _____
_____

Signature: _____ Date: _____ Time: _____

Raw Tissue Assessment Form   FIG. 3

Donor: _____   Date: _____

Inspect tissue:

| | | |
|---|---|---|
| Is the tissue discolored? | ☐ Yes | ☐ No |
| Is there any debris present? | ☐ Yes | ☐ No |
| Does the tissue present any unacceptable odor? | ☐ Yes | ☐ No |
| Tissue shows signs of damage? | ☐ Yes | ☐ No |

*If "Yes" to any questions above, sketch diagram of tissue including notable features:*

Tissue is acceptable for processing:   ☐ Pass   ☐ Fail

Size of tissue: _____ CM X _____ CM

Comments: _____

_____

*Tissue has been assessed according to SOP Raw Tissue Assessment (SB-0205-P) and deemed acceptable for processing.*

Signature: _____   Date: _____

Dehydration Process Form               FIG. 4

| Load Technician: | | Start Date: | / / |
|---|---|---|---|
| | | Start Time: | : |
| Confirm Oven Set Temperature @ 45°C ☐ | | | |
| Enter all Donor Numbers Below ||||
| 01 | ||| 
| 02 | |||
| 03 | |||
| 04 | |||
| 05 | |||
| 06 | |||
| 07 | |||
| 08 | |||
| 09 | |||
| 10 | |||
| Quantity of Tissues Dried: | | Finish Time: | : |
| | | Finish Date: | / / |
| | Total Dehydration Time: | | hours     minutes |
| Residual Moisture Samples Prepared: ☐ ||||
| Unload Technician: | |||
| QA Review: | | Date: | |

PLACENTAL TISSUE GRAFTS

CROSS REFERENCE TO RELATED APPLICATION

This application is a continuation of U.S. patent application Ser. No. 14/222,510, filed on Mar. 21, 2014, which is a continuation of U.S. patent application Ser. No. 13/954,974, filed on Jul. 30, 2013, now U.S. Pat. No. 8,709,494, which is a continuation of U.S. patent application Ser. No. 13/569,095, filed on Aug. 7, 2012, now U.S. Pat. No. 8,597,687, which is a continuation of U.S. patent application Ser. No. 11/840,728, filed on Aug. 17, 2007, now U.S. Pat. No. 8,372,437, which claims the benefit under 35 U.S.C. §119 of U.S. provisional patent application No. 60/838,467, entitled "Method and System for Preserving Amnion Tissue For Later Transplant," filed Aug. 17, 2006. The contents of these applications are incorporated herein by reference in their entireties.

FIELD OF THE INVENTION

The present invention relates generally to tissue allografts and, in particular, to placental membrane tissue grafts (amnion and chorion) and methods of preparing, preserving, and medical uses for the same.

BACKGROUND OF THE INVENTION

Human placental membrane (e.g. amniotic membrane or tissue) has been used for various types of reconstructive surgical procedures since the early 1900s. The membrane serves as a substrate material, more commonly referred to as a biological dressing or patch graft. Such membrane has also been used widely for ophthalmic procedures in the United States and in countries in the southern hemisphere. Typically, such membrane is either frozen or dried for preservation and storage until needed for surgery.

Such placental tissue is typically harvested after an elective Cesarean surgery. The placenta has two primary layers of tissue including amniotic membrane and chorion. The amniotic membrane is a non-vascular tissue that is the innermost layer of the placenta, and consists of a single layer, which is attached to a basement membrane. Histological evaluation indicates that the membrane layers of the amniotic membrane consist of epithelium cells, thin reticular fibers (basement membrane), a thick compact layer, and fibroblast layer. The fibrous layer of amnion (i.e., the basement membrane) contains cell anchoring collagen types IV, V, and VII. The chorion is also considered as part of the fetal membrane; however, the amniotic layer and chorion layer are separate and separable entities.

Amniotic membrane and chorion tissue provide unique grafting characteristics when used for surgical procedures, including providing a matrix for cellular migration/proliferation, providing a natural biological barrier, are non-immunogenic, promote increased self-healing, are susceptible of being fixed in place using different techniques including fibrin glue or suturing. And, such grafts, when properly prepared, can be stored at room temperature for extended periods of time, without need for refrigeration or freezing, until needed for a surgical procedure.

Known clinical procedures or applications for such amnion grafts include Schneiderian Membrane repair (i.e. sinus lift), guided tissue regeneration (GTR), general wound care, and primary closure membrane. Known clinical procedures or applications for such chorion grafts include biological would dressing.

A detailed look at the history and procedure for harvesting and using "live" amniotic tissue for surgical procedures and a method for harvesting and freezing amniotic tissue grafts for ophthalmic procedures is described in U.S. Pat. No. 6,152,142 issued to Tseng, which is incorporated herein by reference in its entirety.

There is a need for improved procedures for harvesting, processing, and preparing amnion and/or chorion tissue for later surgical grafting procedures.

There is a need for improved procedures for processing and preparing multiple layers of amnion and/or chorion tissue for later surgical grafting procedures.

There is a need for preparing and storing such tissue such that the stroma and basement sides of the tissue are easily and quickly identifiable by a surgeon when using such tissue in a surgical procedure.

For these and many other reasons, there is a general need for a method for preparing placenta membrane tissue grafts for medical use, and that includes the steps of obtaining a placenta from a subject, cleaning the placenta, separating the chorion from the amniotic membrane, disinfecting the chorion and/or amniotic membrane, mounting a selected layer of either the chorion or the amniotic membrane onto a drying fixture, dehydrating the selected layer on the drying fixture, and cutting the selected layer into a plurality of tissue grafts. There is an additional need for a drying fixture that includes grooves or raised edges that define the outer contours of each desired tissue graft and that make cutting of the grafts more accurate and easy. There is a further need for a drying fixture that includes raised or indented logos, textures, designs, or text that emboss the middle area of the tissue grafts during dehydration and that enables an end user to be bale to distinguish the top surface from the bottom surface of the graft, which is often necessary to know prior to using such grafts in a medical application or surgical procedure. Such logos, textures, designs, or text can be used for informational purposes or they can, additionally and advantageously, be used for marketing or advertising purposes. There is a need for grafts that are comprised of single layers of amnion or chorion, multiple layers of amnion or chorion, or multiple layers of a combination of amnion and chorion.

The present invention meets one or more of the above-referenced needs as described herein in greater detail.

SUMMARY OF THE INVENTION

One embodiment of the present invention is directed to one or more methods of preparing placenta membrane tissue grafts, comprising the steps of obtaining a placenta from a subject, wherein the placenta includes an amniotic membrane layer and a chorion tissue layer, cleaning the placenta in a solution, separating the chorion tissue layer from the amniotic membrane layer, mounting a selected layer of either the chorion tissue layer or the amniotic membrane layer onto a surface of the drying fixture, dehydrating the selected layer on the drying fixture, and thereafter, cutting the selected layer into a plurality of placenta membrane tissue grafts. The placenta membrane tissue grafts can be either amniotic membrane tissue grafts or chorion tissue grafts. Since amniotic membrane has a stromal side and an opposite, basement side, when dehydrating an amniotic membrane layer, such layer is mounted onto the drying fixture with the basement side facing down and stromal side facing up.

Preferably, the drying fixture includes a texture or design adapted to emboss such texture or design into the placenta membrane tissue grafts during the step of dehydration wherein the texture or design embossed into the placenta membrane tissue enable a user to identify a top and bottom surface of the placenta membrane tissue.

Preferably, the placenta is cleaned in a hypertonic solution wherein the hypertonic solution comprises NaCl concentration in a range of from about 30% to about 10%.

In some embodiments, the method further comprises the step of, after separation of the chorion tissue layer from the amniotic membrane layer, soaking the selected layer in an antibiotic solution. Optionally, the method then also includes the step of rinsing the selected layer to remove the antibiotic solution.

In some embodiments, the method further includes the step of, after separation of the chorion tissue layer from the amniotic membrane layer, physically cleaning the selected layer to remove blood clots and other contaminates.

In other features, the step of dehydrating the selected layer further comprises placing the drying fixture in a breathable bag and heating the bag for a predetermined period of time. Preferably, the bag is heated at a temperature of between 35 degrees and 50 degrees Celcius and the predetermined period of time is between 30 and 120 minutes, wherein 45 degrees Celcius and 45 minutes of time in a non-vacuum over or incubator for a single layer of tissue generally seems ideal.

In one arrangement, the surface of the drying fixture has a plurality of grooves that defines the outer contours of each of the plurality of placenta membrane tissue grafts and wherein the step of cutting comprises cutting the selected layer along the grooves.

In another arrangement, the surface of the drying fixture has a plurality of raised edges that define the outer contours of each of the plurality of placenta membrane tissue grafts and wherein the step of cutting comprises rolling a roller across the top of the selected layer and pressing the selected layer against the raised edges.

In another feature, the method further comprises the step of mounting one or more additional layers of chorion tissue or amniotic layer onto the surface of the drying fixture prior to the step of dehydration to create a plurality of laminated placenta membrane tissue grafts having a thickness and strength greater than a single layer of placenta membrane tissue grafts.

In a further feature, each of the plurality of placenta membrane tissue grafts is rehydrated prior to use of the respective graft for a medical procedure.

In yet further features, the present invention includes tissue grafts processed and prepared according to any of the methods described herein.

In another embodiment, the present invention is directed to a tissue graft that comprises a dehydrated, placenta tissue having a top and bottom surface and an outer contour sized and shaped for use in a suitable medical procedure, wherein a texture or design is embossed within the dehydrated, placenta tissue and wherein the embossment distinguishes the top from the bottom surface of the placenta tissue; and wherein the dehydrated, placenta tissue graft is usable in the suitable medical procedure after being rehydrated. In a feature of this embodiment, the dehydrated, placenta tissue comprises either an amniotic membrane layer or a chorion tissue layer. In yet another feature, the dehydrated, placenta tissue comprises two or more layers of amniotic membrane and chorion tissue, wherein the two or more layers include a plurality of amniotic membrane, a plurality of chorion tissue, or a plurality of amniotic membrane and chorion tissue.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

Further features and benefits of the present invention will be apparent from a detailed description of preferred embodiments thereof taken in conjunction with the following drawings, wherein similar elements are referred to with similar reference numbers, and wherein:

FIG. 1 is a high level flow chart of the primary steps performed in a preferred embodiment of the present invention;

FIG. 2 is an exemplary tissue check-in form used with the preferred embodiment of the present invention;

FIG. 3 is an exemplary raw tissue assessment form used with the preferred embodiment of the present invention;

FIG. 4 is an exemplary dehydration process form used with the preferred embodiment of the present invention;

DETAILED DESCRIPTION OF THE PREFERRED EMBODIMENTS

Figure 5:
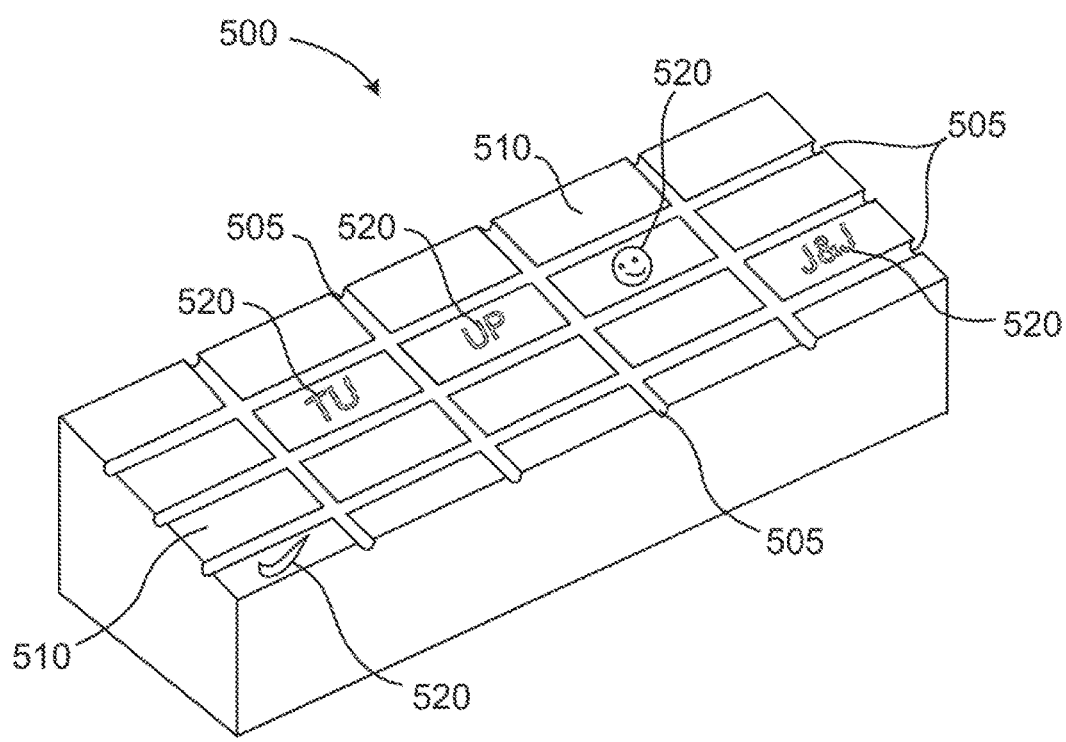
FIG. 5 is a perspective view of an exemplary drying fixture for use with a preferred embodiment of the present invention.

The present invention is more particularly described in the following examples and embodiments that are intended as illustrative only since numerous modifications and variations therein will be apparent to those skilled in the art. Various embodiments of the invention are now described in greater detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which are not intended to influence the scope of the present invention. Additionally, some terms used in this specification are more specifically defined below.

Without intent to limit the scope of the invention, exemplary instruments, apparatus, methods and their related results according to the embodiments of the present invention are given below. Note that titles or subtitles may be used in the discussion of exemplary embodiments of the present invention for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Overview of the Process

Turning first to FIG. 1, a high level overview 100 of the steps undertaken to harvest, process, and prepare placental material for later use as an allograft is disclosed. More detailed descriptions and discussion regarding each individual step will follow. At a high level, initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140), dehydrated (step 150), cut and packaged (step 160), and released (step 170) to the market for use by surgeons and other medical professionals in appropriate surgical procedures and for wound care.

Initial Tissue Collection (Step 110)

The recovery of placenta tissue originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), hepatitis B surface antigens (HBsAg), antibodies to the hepatitis C virus (anti-HCV), antibodies to the human T-lymphotrophic virus type I and type II (anti-HTLV-I and anti-HTLV-II), CMV, and syphilis, using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of, for example, *Clostridium* or *Streptococcus*. If the donor's information, screening tests, and the delivery cultures are all negative (i.e., do not indicate any risks or indicate acceptable level of risk), the donor is approved and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta tissue is collected prior to the completion or obtaining of results from the screening tests and delivery cultures, such tissue is labeled and kept in quarantine. The tissue is approved for further processing only after the required screening assessments and delivery cultures, which declare the tissue safe for handling and use, are satisfied.

Material Check-in and Evaluation (Step 120)

Upon arrival at the processing center or laboratory, the shipment is opened and verified that the sterile shipment bag/container is still sealed and intact, that ice or other coolant is present and that the contents are cool, that the appropriate donor paperwork is present, and that the donor number on the paperwork matches the number on the sterile shipment bag containing the tissue. The sterile shipment bag containing the tissue is then stored in a refrigerator until ready for further processing. All appropriate forms, including a tissue check-in form, such as that shown in FIG. 2, are completed and chain of custody and handling logs (not shown) are also completed.

Gross Tissue Processing (Step 130)

When the tissue is ready to be processed further, the sterile supplies necessary for processing the placenta tissue further are assembled in a staging area in a controlled environment and are prepared for introduction into a critical environment. If the critical environment is a manufacturing hood, the sterile supplies are opened and placed into the hood using conventional sterile technique. If the critical environment is a clean room, the sterile supplies are opened and placed on a cart covered by a sterile drape. All the work surfaces are covered by a piece of sterile drape using conventional sterile techniques, and the sterile supplies and the processing equipments are placed on to the sterile drape, again using conventional sterile technique.

Processing equipment is decontaminated according to conventional and industry-approved decontamination procedures and then introduced into the critical environment. The equipment is strategically placed within the critical environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains, preferably, 18% NaCl (hypertonic saline) solution that is at room or near room temperature. The placenta is gently massaged to help separate blood clots and to allow the placenta tissue to reach room temperature, which will make the separation of the amnion and chorion layers from each other, as discussed hereinafter, easier. After having warmed up to the ambient temperature (after about 10-30 minutes), the placenta is then removed from the sterile processing basin and laid flat on a processing tray with the amniotic membrane layer facing down for inspection.

The placenta tissue is examined and the results of the examination are documented on a "Raw Tissue Assessment Form" similar to that shown in FIG. 3. The placenta tissue is examined for discoloration, debris or other contamination, odor, and signs of damage. The size of the tissue is also noted. A determination is made, at this point, as to whether the tissue is acceptable for further processing.

Next, if the placenta tissue is deemed acceptable for further processing, the amnion and chorion layers of the placenta tissue are then carefully separated. The materials and equipments used in this procedure include the processing tray, 18% saline solution, sterile 4×4 sponges, and two sterile Nalgene jars. The placenta tissue is then closely examined to find an area (typically a corner) in which the amniotic membrane layer can be separated from the chorion layer. The amniotic membrane appears as a thin, opaque layer on the chorion.

With the placenta tissue in the processing tray with the amniotic membrane layer facing down, the chorion layer is gently lifted off the amniotic membrane layer in a slow, continuous motion, using care to prevent tearing of the amniotic membrane. If a tear starts, it is generally advisable to restart the separation process from a different location to minimize tearing of either layer of tissue. If the chorion layer is not needed, it may be gently scrubbed away from the amniotic membrane layer with one of the sterile 4×4 sponges by gently scrubbing the chorion in one direction. A new, sterile 4×4 sponge can be used whenever the prior sponge becomes too moist or laden with the chorion tissue. If the chorion is to be retained, then the separation process continues by hand, without the use of the sponges, being careful not to tear either the amnion layer or the chorion layer.

Care is then taken to remove blood clots and other extraneous tissue from each layer of tissue until the amniotic membrane tissue and the chorion are clean and ready for further processing. More specifically, the amnion and chorion tissues are placed on the processing tray and blood clots are carefully removed using a blunt instrument, a finger, or a sterile non-particulating gauze, by gently rubbing the blood until it is free from the stromal tissue of the amnion and from the trophoblast tissue of the chorion. The stromal layer of the amnion is the side of the amniotic membrane that faces the mother. In contrast, the basement membrane layer is the side of the amnion that faces the baby.

Using a blunt instrument, a cell scraper or sterile gauze, any residual debris or contamination is also removed. This step must be done with adequate care, again, so as not to tear the amnion or chorion tissues. The cleaning of the amnion is complete once the amnion tissue is smooth and opaque-white in appearance. If the amnion tissue is cleaned too much, the opaque layer can be removed. Any areas of the amnion cleaned too aggressively and appear clear will be unacceptable and will ultimately be discarded.

Chemical Decontamination (Step 140)

The amniotic membrane tissue is then placed into a sterile Nalgene jar for the next step of chemical decontamination. If the chorion is to be recovered and processed further, it too is placed in its own sterile Nalgene jar for the next step of chemical decontamination. If the chorion is not to be kept or used further, it can be discarded in an appropriate biohazard container.

Next, each Nalgene jar is aseptically filled with 18% saline solution and sealed (or closed with a top. The jar is then placed on a rocker platform and agitated for between 30 and 90 minutes, which further cleans the tissue of contaminants.

If the rocker platform was not in the critical environment (e.g., the manufacturing hood), the Nalgene jar is returned to the critical/sterile environment and opened. Using sterile forceps, the tissue is gently removed from the Nalgene jar containing the 18% hypertonic saline solution and placed into an empty Nalgene jar. This empty Nalgene jar with the tissue is then aseptically filled with a pre-mixed antibiotic solution. Preferably, the premixed antibiotic solution is comprised of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the tissue. This jar or container containing the tissue and antibiotics is then sealed or closed and placed on a rocker platform and agitated for, preferably, between 60 and 90 minutes. Such rocking or agitation of the tissue within the antibiotic solution further cleans the tissue of contaminants and bacteria.

Again, if the rocker platform was not in the critical environment (e.g., the manufacturing hood), the jar or container containing the tissue and antibiotics is then returned to the critical/sterile environment and opened. Using sterile forceps, the tissue is gently removed from the jar or container and placed in a sterile basin containing sterile water or normal saline (0.9% saline solution). The tissue is allowed to soak in place in the sterile water/normal saline solution for at least 10 to 15 minutes. The tissue may be slightly agitated to facilitate removal of the antibiotic solution and any other contaminants from the tissue. After at least 10 to 15 minutes, the tissue is ready to be dehydrated and processed further.

Dehydration (Step 150)

Next, the now-rinsed tissue (whether it be the amniotic membrane or chorion tissue) is ready to be dehydrated. The amniotic membrane is laid, stromal side down, on a suitable drying fixture. The stromal side of the amniotic membrane is the "tackier" of the two sides of the amniotic membrane. A sterile, cotton tipped applicator may be used to determine which side of the amniotic tissue is tackier and, hence, the stromal side.

The drying fixture is preferably sized to be large enough to receive the tissue, fully, in laid out, flat fashion. The drying fixture is preferably made of Teflon or of Delrin, is the brand name for an acetal resin engineering plastic invented and sold by DuPont and which is also available commercially from Werner Machines, Inc. in Marietta, Ga. Any other suitable material that is heat and cut resistant, capable of being formed into an appropriate shape to receive wet tissue and to hold and maintain textured designs, logos, or text can also be used for the drying fixture. The tissue must be placed on the drying fixture so that it completely covers as many "product spaces" (as explained hereinafter) as possible.

In one embodiment, similar to that shown in FIG. 5, the receiving surface of the drying fixture 500 has grooves 505 that define the product spaces 510, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another embodiment, instead of having grooves to define the product spaces, the drying fixture has raised ridges or blades.

Within the "empty" space between the grooves or ridges, the drying fixture preferably includes a slightly raised or indented texture in the form of text, logo, name, or similar design 520. This textured text, logo, name, or design can be customized or private labeled depending upon the company that will be selling the graft or depending upon the desired attributes requested by the end user (e.g., surgeon). When dried, the tissue will mold itself around the raised texture or into the indented texture—essentially providing a label within the tissue itself. Preferably, such texture/label can be read or viewed on the tissue in only one orientation so that, after drying and cutting, an end user (typically, a surgeon) of the dried tissue will be able to tell the stromal side from the basement side of the dried tissue. The reason this is desired is because, during a surgical procedure, it is desirable to place the allograft in place, with basement side down or adjacent the native tissue of the patient receiving the allograft. FIG. 5 illustrates a variety of marks, logos, and text 520 that can be included within the empty spaces 510 of the drying fixture 500. Typically, a single drying fixture will include the same design or text within all of the empty spaces; however, FIG. 5 shows, for illustrative purposes, a wide variety of designs that can be included on such drying fixtures to emboss each graft.

In a preferred embodiment, only one layer of tissue is placed on the drying fixture. In alternate embodiments, multiple layers of tissue are placed on the same drying fixture to create a laminate-type allograft material that is thicker and stronger than a single layer of allograft material. The actual number of layers will depend upon the surgical need and procedure with which the allograft is designed to be used.

Once the tissue(s) is placed on the drying fixture, the drying fixture is placed in a sterile Tyvex (or similar, breathable, heat-resistant, and sealable material) dehydration bag and sealed. Such breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 and 120 minutes, although approximately 45 minutes at a temperature of approximately 45 degrees Celcius appears to be ideal to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

An appropriate Dehydration recordation form, similar to that shown in FIG. 4, is completed at the end of the dehydration process.

Cutting & Packaging (Step 160)

Once the tissue has been adequately dehydrated, the tissue is then ready to be cut into specific product sizes and appropriately packages for storage and later surgical use. First, the Tyvex bag containing the dehydrated tissue is placed back into the sterile/critical environment. The number of grafts to be produced is estimated based on the size and shape of the tissue on the drying fixture(s). An appropriate number of pouches, one for each allograft, are then also introduced into the sterile/critical environment. The drying fixture(s) are then removed from the Tyvex bag.

If the drying fixture has grooves, then the following procedure is followed for cutting the tissue into product sizes. Preferably, if the drying fixture is configured in a grid pattern, a #20 or similar straight or rolling blade is used to cut along each groove line in parallel. Then, all lines in the perpendicular direction are cut.

If the drying fixture has raised edges or blades, then the following procedure is followed for cutting the tissue into product sizes. Preferably, a sterile roller is used to roll across the drying fixture. Sufficient pressure must be applied so that the dehydrated tissue is cut along all of the raised blades or edges of the drying fixture.

After cutting, each separate piece or tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate graft.

Each tissue graft is then given a final inspection to confirm that there are no tears or holes, that the product size (as cut) is within approximately 1 millimeter (plus or minus) of the specified size for that particular graft, that there are no noticeable blemishes or discoloration of the tissue, and that the textured logo or wording is readable and viewable through the "inner" pouch.

To the extent possible, oxygen is removed from the inner pouch before it is sealed. The inner pouch can be sealed in any suitable manner; however, a heat seal has shown to be effective. Next, each inner pouch is separately packaged in an "outer" pouch for further protection, storage, and shipment.

It should be noted that the above process does not require freezing of the tissue to kill unwanted cells, to decontaminate the tissue, or otherwise to preserve the tissue. The dehydrated allografts are designed to be stored and shipped at room or ambient temperature, without need for refrigeration or freezing.

Product Release (Step 170)

Before the product is ready for shipment and release to the end user, a final inspection is made of both the inner and outer pouches. This final inspection ensure that the allograft contained therein matches the product specifications (size, shape, tissue type, tissue thickness (# of layers), design logo, etc.) identified on the packaging label Each package is inspected for holes, broken seals, burns, tears, contamination, or other physical defects. Each allograft is also inspected to confirm uniformity of appearance, including the absence of spots or discoloration.

Appropriate labeling and chain of custody is observed throughout all of the above processes, in accordance with accepted industry standards and practice. Appropriate clean room and sterile working conditions are maintained and used, to the extent possible, throughout the above processes.

Overview of Clinical Applications

In practice, it has been determined that the above allograft materials can be stored in room temperature conditions safely for at least five (5) years.

When ready for use, such allografts are re-hydrated by soaking them in BSS (buffered saline solution), 0.9% saline solution, or sterile water for 30-90 seconds.

Amnion membrane has the following properties and has been shown to be suitable for the following surgical procedures and indications: Guided Tissue Regeneration (GTR), Schneiderian Membrane repair, primary closure, and general wound care.

Laminated amnion membrane has the following properties and has been shown to be suitable for the following surgical procedures and indications: GTR, Reconstructive, General Wound Care, Neurological, ENT.

Chorion tissue grafts have the following properties and have been shown to be suitable for the following surgical procedures and indications: Biological Dressing or Covering.

Laminated chorion tissue grafts have the following properties and have been shown to be suitable for the following surgical procedures and indications: GTR, Reconstructive, General Wound Care, Neurological, ENT.

Laminated amnion and chorion combined tissue grafts have the following properties and have been shown to be suitable for the following surgical procedures and indications: Advanced Ocular Defects, Reconstructive, General Wound Care, Biological Dressing.

Although the above processes have been described specifically in association with amnion membrane and chorion recovered from placenta tissue, it should be understood that the above techniques and procedures are susceptible and usable for many other types of human and animal tissues. In addition, although the above procedures and tissues have been described for use with allograft tissues, such procedures and techniques are likewise suitable and usable for xenograft and isograft applications.

In view of the foregoing detailed description of preferred embodiments of the present invention, it readily will be understood by those persons skilled in the art that the present invention is susceptible to broad utility and application.

While various aspects have been described in the context of screen shots, additional aspects, features, and methodologies of the present invention will be readily discernable therefrom. Many embodiments and adaptations of the present invention other than those herein described, as well as many variations, modifications, and equivalent arrangements and methodologies, will be apparent from or reasonably suggested by the present invention and the foregoing description thereof, without departing from the substance or scope of the present invention. Furthermore, any sequence(s) and/or temporal order of steps of various processes described and claimed herein are those considered to be the best mode contemplated for carrying out the present invention. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present inventions. In addition, some steps may be carried out simultaneously. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. A dehydrated, laminated bilayer tissue graft consisting of
   a) a washed, cleaned and dehydrated amnion layer isolated from a placenta;
   b) a washed, cleaned and dehydrated chorion layer isolated from a placenta;
   wherein the amnion layer consists of an epithelial cellular layer, a basement membrane, a compact layer, and a fibroblast cellular layer, and further wherein the chorion is in direct contact with the amnion and the two layers are laminated together.

2. The dehydrated, laminated tissue graft of claim 1, wherein the amnion layer and the chorion layer are isolated from the same placenta.

3. The dehydrated, laminated tissue graft of claim 1, wherein one or both of the amnion layer and the chorion layer are treated with an antibiotic prior to lamination.

4. The dehydrated, laminated tissue graft of claim 1, wherein the tissue graft has been exposed to sterilizing conditions.

5. A dehydrated, laminated bilayer tissue graft, wherein the tissue graft consists of an amnion layer and a chorion layer, wherein the amnion layer consists of an epithelial cellular layer, a basement membrane, a compact layer, and a fibroblast cellular layer, and wherein each of the amnion and chorion layers:
   a) is separated from a placenta to provide separated layers of amnion and chorion;
   b) is washed and substantially cleaned while retaining the fibroblast cellular layer on the amnion layer; and
   c) is layered directly over the other and heat dehydrated and laminated to provide the dehydrated, laminated bilayer tissue graft.

6. The dehydrated, laminated tissue graft of claim 5, wherein at least one of the amnion layer or chorion layer has been chemically decontaminated.

7. A dehydrated, laminated placental tissue graft which is a laminate consisting of two washed layers,
   wherein a first of said layers is an amnion layer which consists of an epithelial cellular layer, a basement membrane, a compact layer, and a fibroblast cellular layer, and a second of said layers is (i) amnion that consists of an epithelial cellular layer, a basement membrane, and a compact layer; (ii) amnion that consists of an epithelial cellular layer, a basement membrane, a compact layer, and a fibroblast cellular layer; or (iii) chorion,
   wherein the first and second layers are dehydrated and laminated to each other;
   and wherein the layers were separated prior to being laminated to each other.

* * * * *